US012508166B2

(12) United States Patent
Marcus

(10) Patent No.: US 12,508,166 B2
(45) Date of Patent: Dec. 30, 2025

(54) WOUND BOLSTER DRESSING AND METHOD OF USE

(71) Applicant: Jeffrey R. Marcus, Chapel Hill, NC (US)

(72) Inventor: Jeffrey R. Marcus, Chapel Hill, NC (US)

( * ) Notice: Subject to any disclaimer, the term of this patent is extended or adjusted under 35 U.S.C. 154(b) by 80 days.

(21) Appl. No.: 18/410,147

(22) Filed: Jan. 11, 2024

(65) Prior Publication Data

US 2024/0189154 A1 Jun. 13, 2024

Related U.S. Application Data

(63) Continuation of application No. PCT/US2022/036240, filed on Jul. 6, 2022.

(60) Provisional application No. 63/221,817, filed on Jul. 14, 2021.

(51) Int. Cl.

| | |
|---|---|
| ***A61F 13/01*** | (2024.01) |
| ***A61F 13/00*** | (2024.01) |
| ***A61F 13/05*** | (2024.01) |

(52) U.S. Cl.

CPC .. *A61F 13/01029* (2024.01); *A61F 13/01038* (2024.01); *A61F 13/05* (2024.01); *A61F 2013/00119* (2013.01)

(58) Field of Classification Search

CPC .... A61F 13/05; A61F 13/42; A61F 13/01012; A61F 13/00987; A61F 13/00055; A61F 2013/423; A61F 13/01029; A61F 13/01038; A61F 2013/00119; A61F 13/0206; A61F 2013/00744; A61F 2013/15934; A61F 2013/53062; A61F 13/00008; A61F 13/00021; A61F 2013/00089; A61F 13/00063; A61M 1/90; A61M 1/91; A61M 1/916; A61M 1/917; A61L 2300/00

See application file for complete search history.

(56) References Cited

U.S. PATENT DOCUMENTS

| | | | | |
|---|---|---|---|---|
| 2020/0155361 | A1 | 5/2020 | Pigg et al. | |
| 2020/0163803 | A1 * | 5/2020 | Pigg | A61F 13/05 |
| 2021/0145646 | A1 | 5/2021 | Stephens et al. | |

FOREIGN PATENT DOCUMENTS

| | | | | |
|---|---|---|---|---|
| KR | 20190045179 A | * | 5/2019 | A61B 17/0057 |

OTHER PUBLICATIONS

International Search Report and Written Opinion on PCT PCT/US2022/036240 DTD Nov. 8, 2022 (9 pages).

* cited by examiner

*Primary Examiner* — Ophelia A Hawthorne

(74) *Attorney, Agent, or Firm* — Foley & Lardner LLP

(57) ABSTRACT

A wound bolster includes an inner non-adherent face, a compressible and expandable body, and an outer elastic face where the inner non-adherent face is configured for contact with a wound on a subject and the outer elastic face is configured, upon securing of the wound bolster to a periphery of the wound, to generate a compressive force within the compressible and expandable body in response to applied deformation, which is transmitted as a normal compressive force to the subject.

21 Claims, 6 Drawing Sheets

WOUND BOLSTER DRESSING AND METHOD OF USE

CROSS-REFERENCE TO RELATED APPLICATIONS

The present application is a continuation of International Patent Application No. PCT/US2022/036240 filed Jul. 6, 2022, which claims the benefit of and priority to U.S. Provisional Patent Application No. 63/221,817, filed Jul. 14, 2021, both of which are incorporated herein by reference.

TECHNOLOGY

The present disclosure relates generally to the field of wound dressings, and more specifically, to the use of bolster dressings to facilitate wound healing and/or bridge a transition between one or more wound-associated treatments.

BACKGROUND

Cutaneous wounds are among the most common conditions treated by surgeons. The manner and/or method by which reconstructive repairs are carried out is based on numerous influential factors including: acuity of injury, presence of tissue loss, size, depth, presence of contamination, and exposure of critical structures. In addition to mechanical forces (e.g., sheer forces), wound healing, and specifically engraftment, can be affected by the presence of material/fluid in an interface between a wound bed and a graft. It is for this reason that measures are taken to limit mechanical forces and limit the presence and/or accumulation of materials/fluids in the interface. Biological tissue contours and its movement render difficult the design and implementation of ordinary wound dressings to facilitate wound healing and engraftment. Non-flat (non-planar), mobile, irregularly shaped, convex/concave, and three-dimensional surfaces, such as those present on biological tissue often require that a wound dressing be immobilized relative to the surrounding and/or underlying tissues.

Current designs for wound bolster dressings are often multi-piece constructs that include a plurality of various materials available at the point-of-care. Such wound bolsters often require circumferential placement of numerous suture ties to secure said wound bolster to a subject. As multiple components and/or materials are needed, in addition to requiring an involved coaption process, current wound bolster designs lack standardization and reproducibility. Furthermore, current wound bolster designs are often limited by a size of the wound and become less effective with increasing wound/defect size.

Accordingly, it would be advantageous to provide a wound bolster dressing that protects a wound from environmental elements, limits and/or prevents accumulation of materials and/or fluid within a wound bed, promotes healing, and reduces mechanical forces within the wound area.

SUMMARY

In one aspect, a wound bolster is provided that includes an inner non-adherent face, a compressible and expandable body, and an outer elastic face. The inner non-adherent face is configured for contact with a wound on a subject and the outer elastic face is configured, upon securing of the wound bolster to a periphery of the wound on the subject, to generate a compressive force within the compressible and expandable body in response to an applied deformation that is then transmitted as a normal compressive force to the subject.

In any of the above embodiments, the compressible and expandable body may include at least one elastically responsive first material that is compressible in response to a force and is self-expandable upon a reduction of the force. In any of the above embodiments, the inner non-adherent face may include a first material that is non-adherent to a wound and/or skin of a subject.

In any of the above embodiments, the outer elastic face may include a second material that includes a tear-resistant elastic, wherein the second material may include at least one of a textile, a foam, and a polymer. In any of the above embodiments, the textile may be a multi-ply fabric or a non-woven textile. In any of the above embodiments, the outer elastic face and the inner non-adherent face may be functionally integrated with the compressible and expandable body.

In any of the above embodiments, at least one of the inner non-adherent face, the compressible expandable body, and the outer elastic face may include an antimicrobial agent. In any of the above embodiments, the wound bolster may also include a selectively permeable layer, wherein the layer may include an antimicrobial agent. In any of the above embodiments, the outer elastic face may be configured, upon securing the wound bolster to a periphery of the wound on the subject, to apply a circumferential tension along the periphery of the wound.

In any of the above embodiments, a geometric dimension of the bolster may be adaptable based on a wound size. In any of the above embodiments, at least one of the inner non-adherent face and the compressible and expandable body may adapt to a surface contour of the subject.

In any of the above embodiments, at least one of the inner non-adherent face, the compressible expandable body, and the outer elastic face may enable passage of moisture vapor therethrough. In any of the above embodiments, at least one of the inner non-adherent face, the compressible and expandable body, and the outer elastic face may be configured to facilitate fluid egress from the wound.

In any of the above embodiments, the compressible and expandable body may include a plurality of compressible and expandable layers.

In any of the above embodiments, the outer elastic face may be configured, upon securing of the wound bolster to a periphery of the wound on the subject, to deform with the compressible and expandable body along an outer edge of the wound bolster, and wherein the deformation induces a compressive force to be transmitted from the outer elastic face through the compressible and expandable body and inner non-adherent face and normal to the wound.

According to aspect, a wound bolster kit is provided that includes a wound bolster having an inner non-adherent face, a compressible and expandable body, and an outer elastic face. The inner non-adherent face may be configured for contact with a wound on a subject and the outer elastic face may be configured, upon securing of the wound bolster to a periphery of the wound on the subject, to generate a compressive force within the compressible and expandable body in response to an applied deformation that is then transmitted as a normal compressive force to the subject. The wound bolster may also include a templating device configured to define a circumference of an outer edge of the wound bolster and a coaptation device configured to affix the outer edge to the periphery of the wound. In any of the above embodiments, the coaptation device may be a stapler. In any of the above embodiments, the compressible and expandable body of the wound bolster may include a plurality of compressible and expandable layers.

According to another aspect, a method of affixing a wound bolster to a subject is provided and includes recording a circumference associated with an outer region of a wound area on a subject, altering a size of the wound bolster based on the recorded circumference to form an altered wound bolster, positioning the altered wound bolster on the wound area, and affixing an outer edge of the altered wound bolster to the periphery of the wound area on the subject. In any such embodiments, the method may also include altering the size of the wound bolster to include at least one of changing a thickness and a perimeter associated with the wound bolster. In any such embodiments, the method may also include applying a negative pressure to the wound bolster and the wound area.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

A clear conception of the advantages and features constituting the present disclosure, and of the construction and operation of typical mechanisms provided with the present disclosure, will become more readily apparent by referring to the exemplary, and therefore non-limiting, embodiments illustrated in the drawings accompanying and forming a part of this specification, wherein like reference numerals designate the same elements in the several views, and in which.

Figure 1:
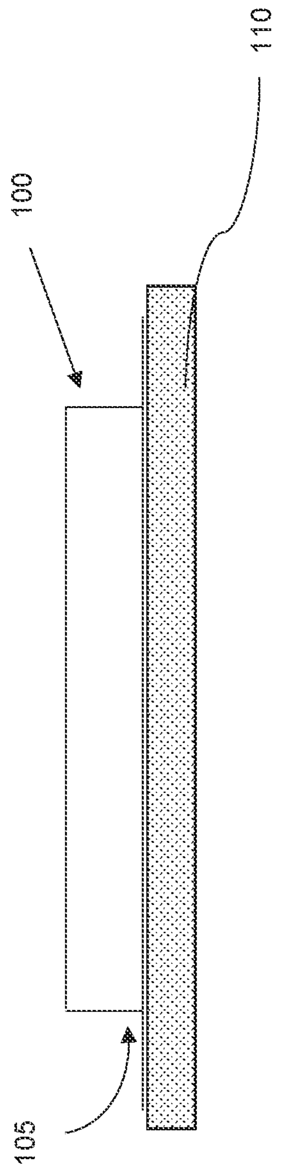
FIG. 1 is a schematic representation of a side view of a wound bolster on a subject, according to one embodiment.

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

DETAILED DESCRIPTION

The foregoing and other features of the present disclosure will become apparent from the following description and appended claims, taken in conjunction with the accompanying drawings. Understanding that these drawings depict only several embodiments in accordance with the disclosure and are therefore, not to be considered limiting of its scope, the disclosure will be described with additional specificity and detail through use of the accompanying drawings.

The present disclosure provides a wound bolster dressing design that not only provides environmental protection, reduction of mechanical forces, mitigation of exudate, and pressure application to a wound, but which is also readily scalable and adaptable to a broad range of wound types and sizes. The present wound bolster dressing includes a standard, reproducible design that consists of a sheet-like structure that can be positioned on/within a wound and circumferentially secured. When deformed along its outer edge, the wound bolster dressing may elastically deform and generate a compressive force along a bottom surface that is in contact with the wound dressing. This assists in wound healing, can assist in adhering of skin grafts to an affected area, and puts pressure on the wound site to assist in keeping out foreign matter from the wound.

The wound bolster dressing is designed such that it is readily scalable, and can be resized to adapt to various wound sizes without necessarily requiring additional components (e.g., added filler). Depending on at the size of the wound sand/or type, the wound bolster dressing can be constructed to have a uniform structure type or the design may be selectable as a modular or laminar structure, having one or more functionally advantageous portions and/or layers to facilitate wound healing.

Referring generally to the figures, a wound bolster dressing includes a main body that is elastically compressible and expandable. The wound bolster dressing further includes an inner face that is non-adherent or has non-adherent characteristics and an outer face that is elastically responsive to applied loads and deformations. The wound bolster is configured such that the inner face is in contact with a wound on a subject and the outer face generates a compressive force within the main body to transmit a normal compressive force to the subject. The wound bolster dressing may include one or more elastically responsive materials that elastically deform and recover when subjected to one or more compressive and/or tensile loads. The wound bolster dressing may include one or more materials with tear-resistant properties. In various embodiments, the wound bolster dressing may include a single material with location-dependent mechanical properties. In other embodiments, the wound bolster dressing may include more than one functionally integrated materials, each having different mechanical properties. The wound bolster dressing may be configured to have a plurality of functionally integrated and/or or laminated layers comprising one or more materials. In various embodiments, the wound bolster dressing may include one or more materials and/or layers that are impregnated with one or more antimicrobial agents.

While much of the disclosure herein is referred to in terms of a "wound bolster dressing," the structures, constructs, kits, and methods described herein may equally apply to any wound dressing or surgical repair materials.

The wound bolster dressing as described herein is adaptable to accommodate wounds of varying sizes. Accordingly, at least one dimension of the wound bolster dressing may be altered to accommodate a wound on a subject. For example, a first dimension of the wound bolster dressing may be altered to accommodate a width or circumference of a wound on a subject, and/or a second dimension of the wound bolster dressing may be altered to accommodate a depth and/or topography of a wound on a subject.

The wound bolster dressing and/or components may be constructed and/or selected based on one or more desirable characteristics. For example, the wound bolster dressing may be constructed and/or selected to include one or more permeable, semi-permeable, and/or non-permeable materials. Alternatively, or in addition, the wound bolster dressing may be constructed and/or selected to include one or more absorbent, semi-absorbent, and/or non-absorbent materials. Where applicable, the wound bolster dressing may be constructed and/or selected to include one or more materials having rigid, semi-rigid, and/or non-rigid characteristics. The wound bolster dressing may be constructed and/or selected to include one or more materials having viscous, viscoelastic, and/or elastic characteristics, and antimicrobial and/or hemostatic characteristics.

The wound bolster dressing may be included within a wound bolster kit, wherein the kit further includes a templating device to facilitate altering a size of the wound bolster dressing and a coaption device to facilitate affixing the wound bolster dressing to a periphery of a wound on a subject.

Figure 2:
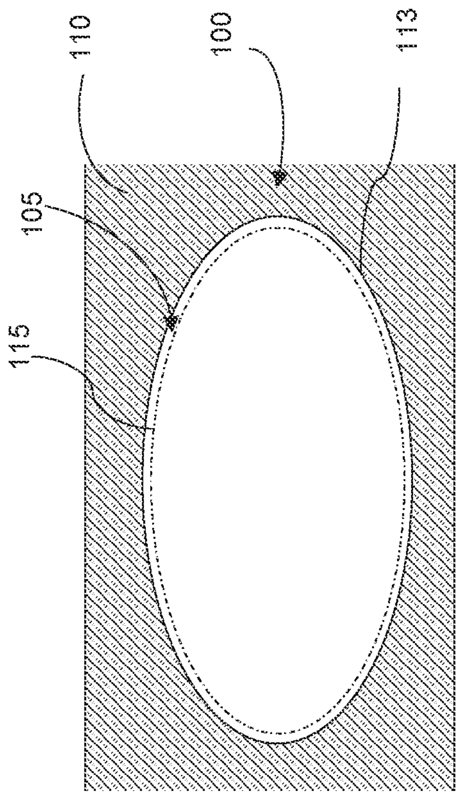
FIG. 2 is a schematic representation of a top view of a wound bolster on a subject, according to one embodiment.

Referring specifically to FIGS. 1 and 2, a wound bolster dressing 100 is illustrated. The wound bolster dressing 100 is positioned at a wound interface 105 on a subject 110. The wound interface 105 is formed by a contacting surface of the wound bolster dressing 100 and a wound surface on a subject 110, which is bound by a wound periphery. In various embodiments, the wound interface 105 may include a wound surface with a constant (e.g., substantially flat or uniform) or varying (e.g., substantially non-flat or non-uniform) topography. As shown, the wound bolster dressing 100 is positioned at a wound interface 105 such that an outer circumference 113 of the wound bolster dressing 100 is within a threshold distance of a periphery 115 of the wound. In various embodiments, the wound bolster dressing 110 may be positioned relative to the wound interface 105 such that the circumference 113 of the wound bolster dressing 100 is coincident with the periphery 115 of the wound on the subject. In various embodiments, the circumference 113 of the wound bolster dressing 100 may be larger than the periphery 115 of the wound.

Figure 3:
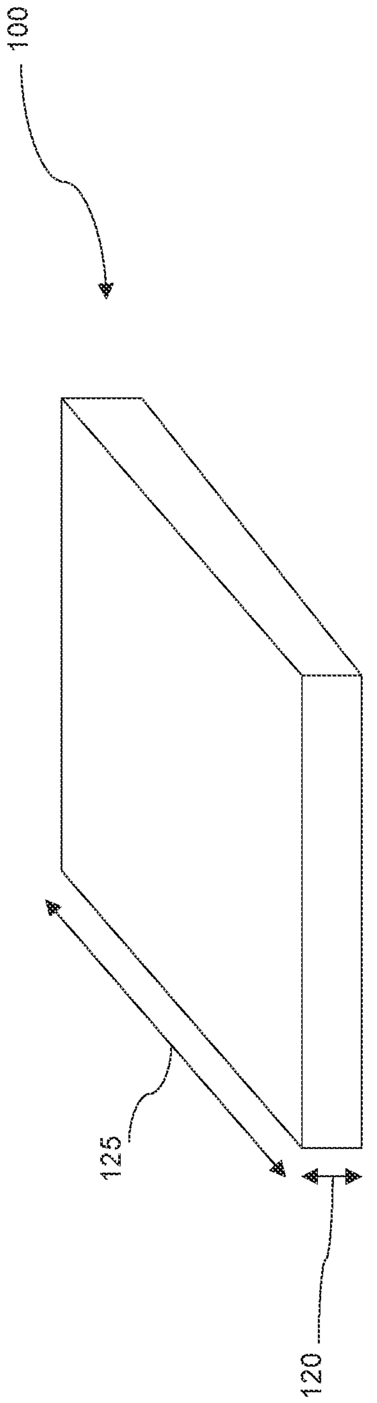
FIG. 3 is a schematic representation of a perspective view of a wound bolster, according to one embodiment.
Figure 4:
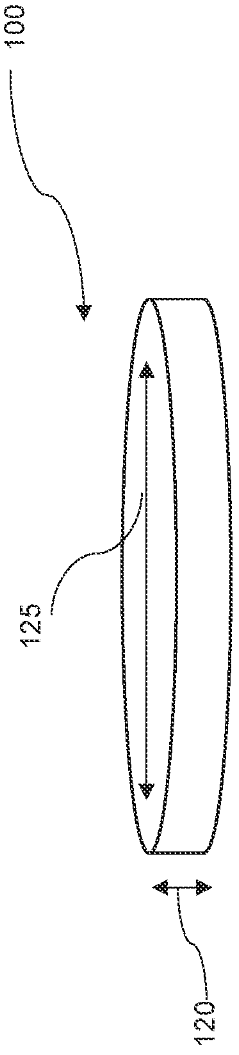
FIG. 4 is a schematic representation of a perspective view of a wound bolster, according to one embodiment.

FIGS. 3 and 4 show schematic perspective views, respectively, of a wound bolster dressing 100, according to various exemplary embodiments. As shown, a size of a wound bolster dressing 100 may be defined by one or more dimensions that may include a substantially vertical first dimension 120 (e.g., thickness) and one or more substantially horizontal second dimensions 125 (e.g., length, width, diameter). FIG. 3 shows the wound bolster dressing 100 having a first dimension 120 and a second dimension 125, which correspond to a thickness and length, respectively. FIG. 4 shows a wound bolster dressing 100 having a first dimension 120 and a second dimension 125, which correspond to a thickness and width and/or diameter, respectively. In various embodiments, at least one of the first and the second dimensions may be alterable based on at least one of the wound periphery (e.g., periphery 115) and one or more characteristics associated with the wound surface on the subject. The one or more characteristics associated with the wound surface may include, but are not limited to, a depth of the wound, a topography of the wound, a type of wound, an amount or type of fluid produced by the wound, a location of the wound on the subject 110, and a wound treatment type. In various implementations, the depth of the wound is determined as a normal distance from a plane defined by the periphery 115 of the wound to a point located on the wound surface. In various implementations, the topography of the wound may be characterized as smooth, even, uneven, ridged, and/or rough, wherein the characterization may be determined based on a visual assessment and/or a quantitative assessment of asperities of the wound surface.

Wounds typically are unique, and the wound bolster dressing 100 can be configured to adapt to a wide variety of wound and wound interfaces 105 on subjects 110. The wound bolster dressing 100 may have first and second dimensions 120 and 125, respectively, to accommodate varying wound peripheries 113. Furthermore, the wound bolster dressing 100 may also accommodate varying wound types and topographies based on one or more mechanical characteristics of the wound bolster dressing 100.

Figure 5:
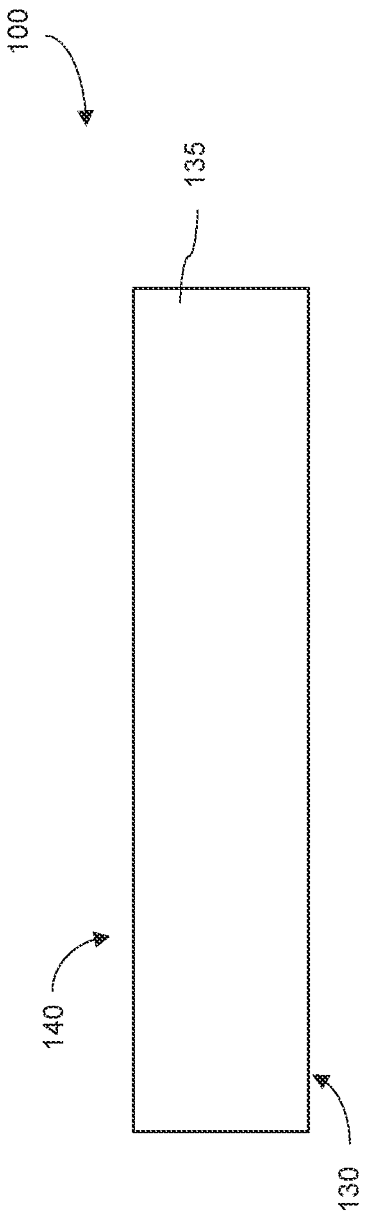
FIG. 5 is a schematic representation of a side view of a wound bolster, according to one embodiment.

FIG. 5 shows a schematic side view of a wound bolster dressing 100 that includes a main body 135 having an inner first face 130 and an outer second face 140. In various embodiments, the first face 130 is configured to contact a wound at a wound interface 105 on a subject 110. The main body 135 may be configured to be elastically responsive to applied compressive, tensile, and/or torsional loads. In various embodiments, the main body 135 is compressible and expandable such that it deforms in response to an applied compressive load and expands in response to a reduction of said compressive load. The main body 135 may include one or more elastically responsive materials, for example, a composite material, a textile, a foam, and/or a polymer.

The main body 135 may be configured to generate a compressive force therein responsive to an applied load or deformation on or along the second face 140 and, consequently, cause the compressive load to be transmitted normal to the first face 130. In various embodiments wherein wound bolster dressing 100 is positioned at wound interface 105, an applied load or deformation along second face 140 causes a compressive force to be generated within main body 135, which is then transmitted normal to the first face 130 as a compressive force on or along the wound surface within the wound interface 105. The compressive force transmitted normal to the first face 130 enables the wound bolster dressing 100 to adapt to the wound surface by forming to the various features of the wound surface as it compresses the surface. Furthermore, in various embodiments, the main body 135 of the wound bolster dressing 100 may be configured to generate an internal load responsive to a deformation, wherein the deformation may be applied during fixation of the wound bolster dressing 100 at the wound interface 105 on the subject 110. Consequently, the wound bolster dressing 100 may be configured to cause a circumferential tension along the periphery 115 of the wound on the subject 110.

The first face 130 may be non-adherent or have non-adherent characteristics to inhibit adherence of wound bolster dressing 100 to the wound interface 105. For example, the first face 130 may be coated with one or more non-adherent substances, or it may be include one or more materials having non-adherent properties. The second face 140 may have elastic and tear resistant properties, for example, it may include at least one of a foam, a textile, and a polymer that is tear-resistant. Where a foam is used, it may include a closed-cell foam, an open-cell foam, or a combination thereof. The one or more textiles may include a single-ply fabric, a multi-ply fabric, a non-woven textile, or a combination thereof. The one or more polymers may include a natural polymer, a synthetic polymer, a semi-synthetic polymer, or a combination thereof.

In various embodiments, at least one of the first face 130, the second face 140, and the main body 135 of the wound bolster dressing 100 may include one or more antimicrobial and/or hemostatic agents. For example, the wound bolster dressing 100 or a component thereof may be impregnated with the one or more antimicrobial and/or hemostatic agents. In various embodiments, the wound bolster dressing 100 or a component thereof may be selectively permeable, wherein at least one of fluid (e.g., wound discharge), gas (e.g., ambient air), and vapor may selectively pass through the wound bolster dressing 100. In various embodiments, at least one of the first face 130, the second face 140, and the main body 135 may facilitate fluid egress at the wound interface 105.

Figure 6:
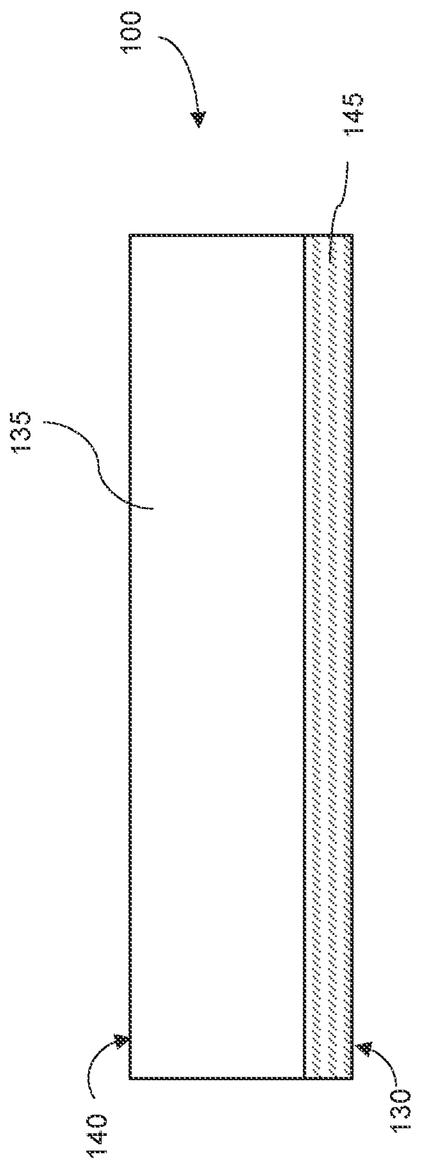
FIG. 6 is a schematic representation of a side view of a wound bolster, according to one embodiment.
Figure 7:
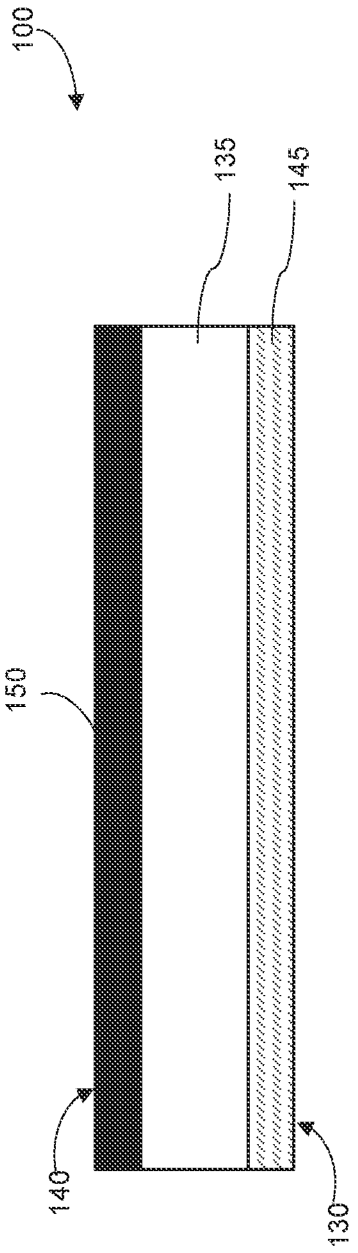
FIG. 7 is a schematic representation of a side view of a wound bolster, according to one embodiment.
Figure 8:
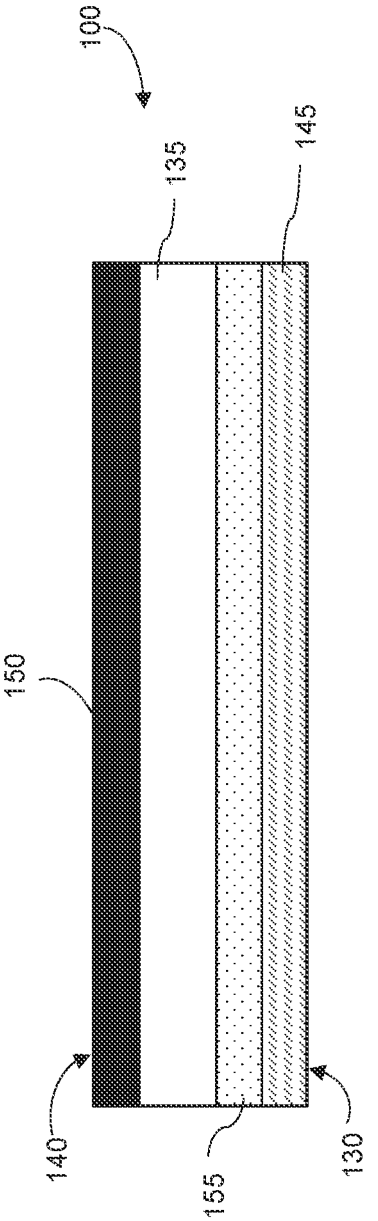
FIG. 8 is a schematic representation of a side view of a wound bolster, according to one embodiment.

The wound bolster dressing 100 may include one or more layers. FIGS. 6-8 show schematic side perspective views of a wound bolster dressing 100. As shown in FIG. 6, wound bolster dressing 100 may have a first face 130 and a second face 140, which are configured to contact the wound interface 105 and an ambient environment, respectively. The wound bolster dressing 100 may include a main body 135 and an inner layer 145, which is functionally integrated with the main body 135 and the inner first face 130. In various embodiments, each of the main body 135 and the inner layer 145 may include one or more materials. For example, the inner layer 145 may include one or more materials that are mechanically (e.g., elastic modulus), structurally (e.g., woven, non-woven, cell-structure), and/or characteristically (e.g., porosity, permeability, antimicrobial properties) similar to one or more materials within the main body 135. In some embodiments, main body 135 and layer 145 may be mutually coupled, laminated, or otherwise conjoined. In some embodiments, main body 135 and layer 145 may be separate components and instead may engage across a shared interface therebetween.

In various embodiments, the wound bolster dressing 100 may include materials that exhibit mechanically (e.g., elastic modulus), structurally (e.g., woven, non-woven, cell-structure), and/or characteristically (e.g., porosity, permeability, antimicrobial properties) advantageous properties according to one or more predetermined desirable characteristics. For example, the wound bolster dressing 100 may include one or more materials with a specific degree of permeability to facilitate egress of biological fluids (e.g., blood, serum, wound exudate, etc.) from the wound interface 105. Such a wound bolster dressing 100 could be used together with one or more wound dressings, wherein the wound bolster dressing 100 could draw fluid away from the wound interface 105, enable breathability (i.e., air passage) through the wound bolster dressing 100 and a co-located wound dressing, and provide protection and stability to the wound interface 105. Alternatively or in addition, the wound bolster dressing 100 may include one or more materials with a specific degree of porosity and/or permeability to enable delivery of one or more medical agents (e.g., antimicrobial agent) through topical application to the wound bolster dressing 100, wherein the wound bolster dressing 100 would allow the delivered one or more medical agents to permeate through to the wound interface 105.

As illustrated in FIG. 7, a wound bolster dressing 100 may further include an outer layer 150, which is functionally integrated with the main body 135 and the outer second face 140. In various embodiments, the outer layer 150 may include one or more materials that are mechanically, structurally, and/or characteristically similar to one or more materials within at least one of the main body 135 and the inner layer 145. In some embodiments, main body 135, inner layer 145, and/or outer layer 150 may be mutually coupled, laminated, or otherwise conjoined. In some embodiments, at least one of main body 135, inner layer 145, and outer layer 150 may be mutually unattached and instead may engage across one or more shared interfaces therein.

The wound bolster dressing 100 may include any number of layers disposed between the inner first face 130 and the outer second face 140, the main body 135 within wound bolster dressing 100 may, itself, comprise one or more layers. As shown in FIG. 8, wound bolster dressing 100 may further include an intermedial layer 155, disposed between inner layer 145 and outer layer 150. The intermedial layer 155 is functionally integrated with the main body 135 and the inner layer 145. In various other embodiments, intermedial layer 155 may be disposed proximate to the outer layer 150 and be functionally integrated with the main body 135 and the outer layer 150. In various embodiments, the intermedial layer 155 may include one or more materials that are mechanically, structurally, and/or characteristically similar to one or more materials within at least one of the main body 135, the inner layer 145, and the outer layer 150. In some embodiments, main body 135, inner layer 145, outer layer 150, and/or intermedial layer 155 may be mutually coupled, laminated, or otherwise conjoined. In some embodiments, at least one of main body 135, inner layer 145, outer layer 150, and intermedial layer 155 may be mutually unattached and instead may engage across one or more shared interfaces therein. The intermedial layer 155 may be encompassed within the main body 135. While FIGS. 6, 7, and 8 show a wound bolster dressing 100 having two, three, and four layers, respectively, various other embodiments may include any number of functionally integrated layers within wound bolster dressing 100. In various embodiments, a number of layers within wound bolster dressing 100 may be based, at least in part, on a size, type, and/or topography of a wound on a subject 110. In various embodiments, one or more desired mechanical, structural, and/or functional characteristics of wound bolster 100 may determine a number and/or type of layers included therein.

Figure 9:
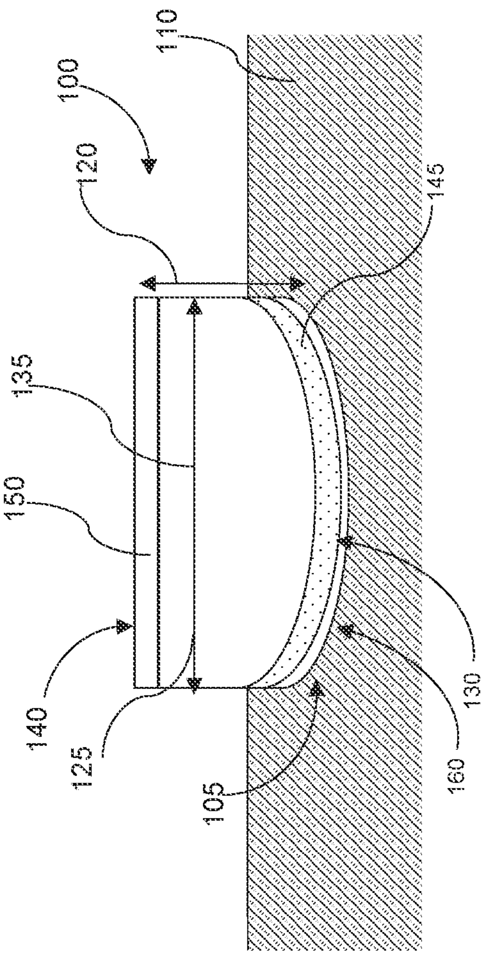
FIG. 9 is a schematic representation of a side cross-sectional view of a wound bolster positioned within a wound bed on a subject, according to one embodiment.

FIG. 9 shows a schematic side perspective view of a wound bolster dressing 100 positioned at a wound interface 105 on a subject 110. In various implementations related to use of wound bolster dressing 100, parameters associated with wound interface 105, including at least one of a circumference of a wound periphery (e.g., periphery 115) and wound depth, may be determined. The determined one or more parameters may be used to further determine at least one of a first dimension 120 and a second dimension 125 for wound bolster dressing 100. The one or more templates and/or templating devices may be used to the first and second dimensions 120 and 125, respectively, based on one or more wound interface 105 parameters. The one or more templates and/or templating devices may include a transparent component to allow for tracing of an outer periphery 115 of the wound interface 105. In various embodiments, the one or more templates and/or templating devices may be partially or wholly consumed and/or disposed during or after use. In various embodiments, the one or more templates may be integrated with the wound bolster dressing 100. In various embodiments, wound bolster dressing 100 may be altered to have first and second dimensions 120 and 125, respectively. In other embodiments, wound bolster dressing 100 may have a predetermined first and second dimensions 120 and 125, which correspond to a range of wound interface 105 parameters.

After determining necessary the first and second dimensions 120 and 125, respectively, based on a parameter associated with the wound interface 105, the wound bolster dressing 100 may be first positioned at the wound interface 105. As shown, the wound bolster dressing 100 includes inner layer 145, main body 135, and outer layer 150, which are disposed between inner first face 130 and outer second face 140. Though FIG. 9 shows the wound bolster dressing 100 as having three layers, the wound bolster dressing 100 may include any number of layers, according to various exemplary embodiments. As illustrated, the inner first face 130, which is functionally integrated and/or interfaced with inner layer 145, is configured to contact wound surface 160. Conversely, the outer second face 140, which is functionally integrated and/or interfaced with the outer layer 150, is configured for exposure with an ambient environment.

Figure 10:
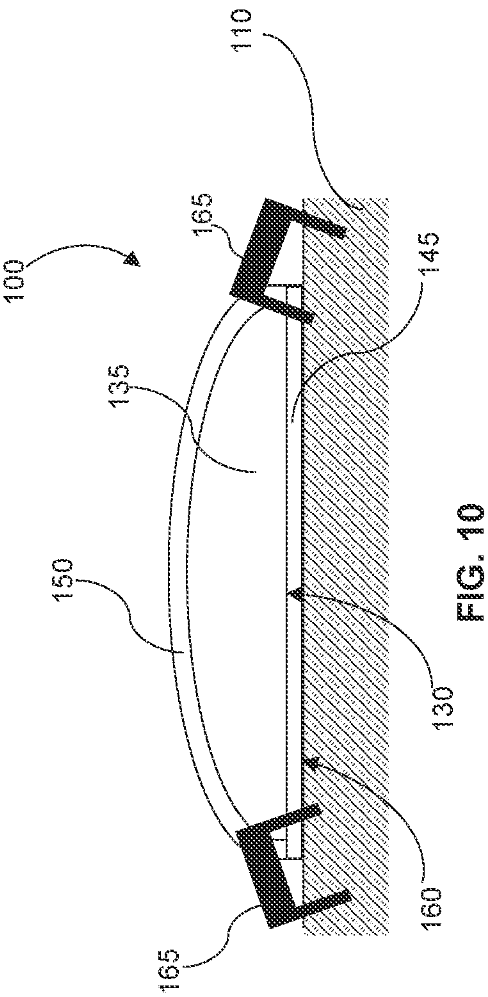
FIG. 10 is a schematic representation of a side cross-sectional view of a wound bolster coapted to a periphery of a wound on a subject, according to one embodiment.
Figure 11:
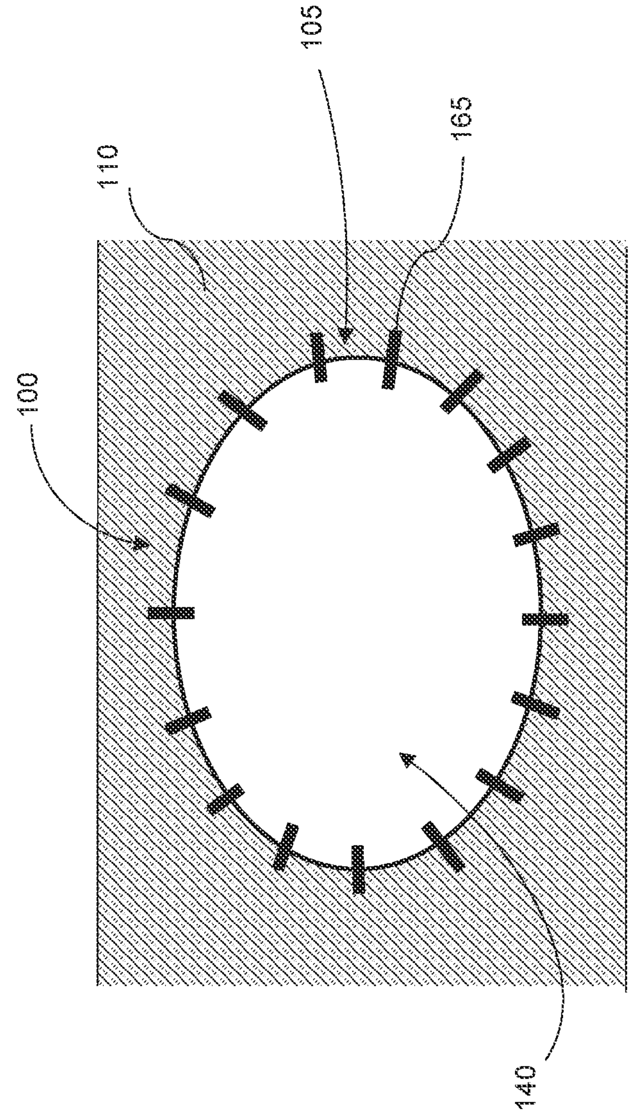
FIG. 11 is a schematic representation of a top view of a wound bolster coapted to a periphery of a wound on a subject, according to one embodiment.

After the wound bolster dressing 100 is positioned at the wound interface 105, it may be affixed or coapted to the subject 110 along an outer edge (e.g., along circumference 113) of the wound bolster dressing 100 and near the periphery 115 of the wound interface 105. FIG. 10 shows a schematic side cross-sectional view of the wound bolster dressing 100 affixed to subject 110, according to an exemplary embodiment. As shown, the implements 165 are disposed near an outer edge of the wound bolster dressing 100 and facilitate fixation of the wound bolster dressing to the subject 110. In various embodiments, implements 165 may include surgical sutures, staples, or any other coaptation implement known in the art. In various embodiments, implements 165 may be applied to wound bolster dressing 100 using one or more coaptation devices including, but not limited to, a surgical stapler (e.g., septal stapler). FIG. 11 shows a schematic top view of a wound bolster dressing 100 affixed to a subject 110 near a wound interface 105. As shown, a plurality of implements 165 may be applied to wound bolster dressing 100 to facilitate fixation to the subject 110.

The wound bolster dressing 100 may be configured to integrate with a negative pressure wound system. Negative pressure systems are configured to actively remove exudate from a wound area. Such systems generally require sealing a wound dressing (e.g., via film application) and fluidly coupling a vacuum pump (e.g., via tubing) to facilitate exudate removal. Typically, a negative pressure system can be applied over a variety of wound dressing types with sufficient permeability to allow exudate flow therethrough. In various embodiments, the wound bolster dressing 100 may include one or more materials having sufficient permeability to allow exudate to be removed from the wound region 105. Consequently, the wound bolster dressing 100 can be fixed to the subject 110, sealed, and coupled to a negative pressure wound system. Removal of exudate and/or fluid from the wound interface 105 may consequently enable prolonged fixation of wound bolster dressing 100 to subject 110. In various implementations, the negative pressure system can be uncoupled from the wound bolster dressing 100 and the wound bolster dressing 100 can remain fixed to the subject 110 to facilitate continued wound healing thereafter.

Fixation of wound bolster dressing 100 to the subject 110 results in an applied displacement and subsequent generation of tension along outer second face 140. The induced tension consequently causes an induced compression within main body 135 and in any layers functionally integrated or interfaced therewith (e.g., layers 145, 150). The applied displacement via fixation of wound bolster dressing 100 to subject 110 may also induce a circumferential tension within outer second face 140. The generated compression is transmitted and applied at the wound interface 105 along wound surface 160 and inner first face 130. Likewise, induced tension within the outer second face 140 may also cause a circumferential tension along the periphery 115 of the wound interface 105. Compression at the wound interface 105 facilitates prevention and/or reduction of fluid production therein. Furthermore, compression at the wound interface 105 reduces displacement and/or deformation of tissue within a wound area on the subject 110 as the applied compression may immobilize surrounding tissue.

In various embodiments, any of the wound bolster dressings as described herein may be included within a wound bolster dressing kit. In various embodiments, the wound bolster dressing kit may include one or more wound bolster dressings 100, one or more templates and/or templating devices configured to facilitate determination of at least one of the first dimension 120 and second dimension 125, and one or more coaptation devices configured to affix the wound bolster dressing 100 to a subject 110 along or near a periphery 115 of a wound interface 105. In various embodiments, a wound bolster dressing kit may include a plurality of wound bolster dressings 100, wherein each of the wound bolster dressings 100 may have predetermined first and second dimensions 120 and 125 that correspond to various ranges of wound interface 105 parameters. In some embodiments, a wound bolster dressing kit may further include one or more layers, which are configured to integrate and/or interface with the one or more wound bolster dressings 100. In various embodiments, the one or more layers may be mechanically, structurally, and/or functionally similar, different, or a combination thereof.

Notwithstanding the embodiments described above in FIGS. 1-11, various modifications and inclusions to those embodiments are contemplated and considered within the scope of the present disclosure.

It is also to be understood that the construction and arrangement of the elements of the systems and methods as shown in the representative embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed.

Accordingly, all such modifications are intended to be included within the scope of the present disclosure. Any means-plus-function clause is intended to cover the structures described herein as performing the recited function and not only structural equivalents but also equivalent structures. Other substitutions, modifications, changes, and omissions may be made in the design, operating conditions, and arrangement of the preferred and other illustrative embodiments without departing from scope of the present disclosure or from the scope of the appended claims.

Furthermore, functions and procedures described above may be performed by specialized equipment designed to perform the particular functions and procedures. The functions may also be performed by general-use equipment that executes commands related to the functions and procedures, or each function and procedure may be performed by a different piece of equipment with one piece of equipment serving as control or with a separate control device.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to disclosures containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances, where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

Moreover, although the figures show a specific order of method operations, the order of the operations may differ from what is depicted. In addition, two or more operations may be performed concurrently or with partial concurrence. Such variation will depend on hardware systems chosen and on designer choice. All such variations are within the scope of the disclosure.

What is claimed is:

1. A wound bolster comprising:
an inner non-adherent face;
a compressible and expandable body;
an outer elastic face; and
at least one layer disposed between the compressible and expandable body and the inner non-adherent face, the at least one layer being mutually uncoupled from the compressible and expandable body and the inner non-adherent face;
wherein:
the inner non-adherent face is configured for contact with a wound on a subject; and
the outer elastic face is configured, upon securing of the wound bolster to a periphery of the wound on the subject, to generate a compressive force within the compressible and expandable body in response to an applied deformation that is then transmitted as a normal compressive force to the subject.

2. The wound bolster of claim 1, wherein the outer elastic face comprises a second material comprising a tear-resistant elastic and wherein the second material comprises at least one of a textile, a foam, and polymer.

3. The wound bolster of claim 2, wherein the textile is selected from a multi-ply fabric and a non-woven textile.

4. The wound bolster of claim 1, wherein the compressible and expandable body comprises at least one elastically responsive first material that is compressible in response to a force and is self-expandable upon a reduction of the force.

5. The wound bolster of claim 1, wherein the inner non-adherent face comprises a first material that is non-adherent to a wound and/or skin of a subject.

6. The wound bolster of claim 1, wherein the outer elastic face and the inner non-adherent face are functionally integrated with the compressible and expandable body.

7. The wound bolster of claim 1, wherein at least one of the inner non-adherent face, the compressible expandable body, and the outer elastic face comprises an antimicrobial agent.

8. The wound bolster of claim 1, further comprising a selectively permeable layer, wherein the layer comprises an antimicrobial agent.

9. The wound bolster of claim 1, wherein the outer elastic face is further configured, upon securing the wound bolster to a periphery of the wound on the subject, to apply a circumferential tension along the periphery of the wound.

10. The wound bolster of claim 1, wherein at least one of the inner non-adherent face and the compressible and expandable body adapts to a surface contour of the subject.

11. The wound bolster of claim 1, wherein at least one of the inner non-adherent face, the compressible expandable body, and the outer elastic face enables passage of moisture vapor therethrough.

12. The wound bolster of claim 1, wherein the compressible and expandable body comprises a plurality of compressible and expandable layers.

13. The wound bolster of claim 1, wherein at least one of the inner non-adherent face, the compressible and expandable body, and the outer elastic face is configured to facilitate fluid egress from the wound.

14. The wound bolster of claim 1, wherein the outer elastic face is configured, upon securing of the wound bolster to a periphery of the wound on the subject, to deform with the compressible and expandable body along an outer edge of the wound bolster, and wherein the deformation induces a compressive force to be transmitted from the outer elastic face through the compressible and expandable body and inner non-adherent face and normal to the wound.

15. The wound bolster of claim 1, wherein at least one of the inner-non-adherent face, the compressible and expandable body, or the outer elastic face comprises a hemostatic agent.

16. A wound bolster kit comprising:
- a wound bolster, wherein the wound bolster comprises:
  - an inner non-adherent face;
  - a compressible and expandable body;
  - an outer elastic face; and
  - at least one layer disposed between the compressible and expandable body and the inner non-adherent face, the at least one layer being mutually uncoupled from the compressible and expandable body and the inner non-adherent face
  - wherein:
    - the inner non-adherent face is configured for contact with a wound on a subject; and
    - the outer elastic face is configured, upon securing of the wound bolster to a periphery of the wound on the subject, to generate a compressive force within the compressible and expandable body in response to an applied deformation that is then transmitted as a normal compressive force to the subject;
- a templating device configured to define a circumference of an outer edge of the wound bolster; and
- a coaptation device configured to affix the outer edge to the periphery of the wound.

17. The wound bolster kit of claim 16, wherein the coaptation device is a stapler.

18. The wound bolster kit of claim 16, wherein the compressible and expandable body of the wound bolster comprises a plurality of compressible and expandable layers.

19. A method of affixing a wound bolster to a subject, the method comprising:
- recording a circumference associated with an outer region of a wound area on a subject;
- altering a size of the wound bolster based on the recorded circumference to form an altered wound bolster;
- positioning the altered wound bolster on the wound area; and
- affixing an outer edge of the altered wound bolster to the periphery of the wound area on the subject;
- wherein the wound bolster comprises:
  - an inner non-adherent face configured for contact with the wound area;
  - a compressible and expandable body; and
- an outer elastic face configured to generate a compressive force within the compressible and expandable body in response to an induced tension; and
  - at least one layer disposed between the compressible and expandable body and the inner non-adherent face, the at least one layer being mutually uncoupled from the compressible and expandable body and the inner non-adherent face;
  - and
- wherein affixing the wound bolster induces tension within the elastic outer face that causes the wound bolster to exert the compressive force on the wound area.

20. The method of claim 19, wherein altering the size of the wound bolster comprises at least one of changing a thickness or changing a perimeter associated with the wound bolster.

21. The method of claim 19, further comprising applying a negative pressure to the wound bolster and the wound area.

* * * * *